United States Patent
Blumenkranz et al.

(10) Patent No.: US 11,666,243 B2
(45) Date of Patent: *Jun. 6, 2023

(54) SYSTEMS AND METHODS FOR REDUCING MEASUREMENT ERROR USING OPTICAL FIBER SHAPE SENSORS

(71) Applicant: INTUITIVE SURGICAL OPERATIONS, INC., Sunnyvale, CA (US)

(72) Inventors: Stephen J. Blumenkranz, Los Altos, CA (US); Caitlin Q. Donhowe, Mountain View, CA (US); Randall L. Schlesinger, San Mateo, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 987 days.

This patent is subject to a terminal disclaimer.

(21) Appl. No.: 16/410,710

(22) Filed: May 13, 2019

(65) Prior Publication Data

US 2019/0343424 A1    Nov. 14, 2019

Related U.S. Application Data

(63) Continuation of application No. 14/879,291, filed on Oct. 9, 2015, now Pat. No. 10,314,513.
(Continued)

(51) Int. Cl.
*A61B 5/06* (2006.01)
*A61B 1/005* (2006.01)
(Continued)

(52) U.S. Cl.
CPC ............ *A61B 5/065* (2013.01); *A61B 1/0051* (2013.01); *A61B 5/1076* (2013.01);
(Continued)

(58) Field of Classification Search
CPC ..... A61B 5/065; A61B 1/0051; A61B 5/1076; A61B 5/6852; A61B 5/6855; A61B 5/05;
(Continued)

(56) References Cited

U.S. PATENT DOCUMENTS

4,695,697 A * 9/1987 Kosa ...................... A61B 18/20
385/94
6,171,297 B1  1/2001 Pedersen et al.
(Continued)

OTHER PUBLICATIONS

Mottu F., et al., "Radiopaque Polymeric Materials for Medical Applications: Current Aspects of Biomaterial Research," Investigative Radiology, May 1999, vol. 34 (5), 10 pages.
(Continued)

*Primary Examiner* — Sanjay Cattungal
(74) *Attorney, Agent, or Firm* — Haynes and Boone, LLP

(57) ABSTRACT

An apparatus includes an instrument that comprises an elongated, flexible body including an inner surface and an outer surface, wherein the inner surface is shaped to define a lumen extending through at least a portion of the elongated, flexible body. The instrument further comprises a plurality of portions extending along a length of the elongated, flexible body. The apparatus further comprises a radiopaque material incorporated into a first portion of the plurality of portions and a second portion of the plurality of portions, wherein the radiopaque material is incorporated into the first portion such that the first portion has a first radiopacity, and the radiopaque material is incorporated into the second portion such that the second portion has a second radiopacity, wherein the first radiopacity is different from the second radiopacity.

20 Claims, 8 Drawing Sheets

Related U.S. Application Data

(60) Provisional application No. 62/062,304, filed on Oct. 10, 2014.

(51) Int. Cl.
*A61B 5/00* (2006.01)
*A61B 5/107* (2006.01)
*A61B 34/20* (2016.01)
*A61B 5/05* (2021.01)

(52) U.S. Cl.
CPC .......... *A61B 5/6852* (2013.01); *A61B 5/6855* (2013.01); *A61B 5/05* (2013.01); *A61B 5/066* (2013.01); *A61B 2034/2061* (2016.02); *A61B 2562/0233* (2013.01)

(58) Field of Classification Search
CPC ............ A61B 5/066; A61B 2034/2061; A61B 2562/0233
See application file for complete search history.

(56) References Cited

U.S. PATENT DOCUMENTS

| | | | |
|---|---|---|---|
| 6,380,732 B1 | 4/2002 | Gilboa et al. | |
| 6,389,187 B1 | 5/2002 | Greenaway et al. | |
| 6,652,692 B2 | 11/2003 | Pedersen et al. | |
| 7,329,223 B1 | 2/2008 | Ainsworth et al. | |
| 7,532,920 B1 | 5/2009 | Ainsworth et al. | |
| 7,772,541 B2 * | 8/2010 | Froggatt ............ | G02B 6/02042 250/226 |
| 7,781,724 B2 * | 8/2010 | Childers ............ | A61B 1/00165 250/227.14 |
| 7,930,065 B2 | 4/2011 | Larkin et al. | |
| 8,900,131 B2 * | 12/2014 | Chopra .................. | A61B 1/009 600/407 |
| 9,066,739 B2 | 6/2015 | Larkin et al. | |
| 9,743,992 B2 * | 8/2017 | Stigall .................... | A61B 90/39 |
| 10,314,513 B2 | 6/2019 | Blumenkranz et al. | |
| 2006/0013523 A1 | 1/2006 | Childlers et al. | |
| 2007/0185476 A1 * | 8/2007 | Maksimovich ........ | A61B 18/24 606/2 |
| 2007/0191708 A1 | 8/2007 | Gerold et al. | |
| 2008/0319266 A1 | 12/2008 | Poll et al. | |
| 2009/0318835 A1 * | 12/2009 | Ressemann ........... | A61M 25/09 600/585 |
| 2010/0168520 A1 | 7/2010 | Poll et al. | |
| 2010/0198014 A1 | 8/2010 | Poll et al. | |
| 2012/0022331 A1 | 1/2012 | Poll et al. | |
| 2012/0165610 A1 | 6/2012 | Poll et al. | |
| 2012/0184897 A1 | 7/2012 | Poll | |
| 2012/0197084 A1 | 8/2012 | Drach et al. | |
| 2012/0289777 A1 * | 11/2012 | Chopra ............ | A61B 1/000094 382/128 |
| 2012/0310147 A1 | 12/2012 | Poll et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR REDUCING MEASUREMENT ERROR USING OPTICAL FIBER SHAPE SENSORS

RELATED APPLICATIONS

This patent application is a continuation of U.S. patent application Ser. No. 14/879,291, filed Oct. 9, 2015, which claims priority to and the benefit of the filing date of U.S. Provisional Patent Application 62/062,304, filed Oct. 10, 2014, entitled "SYSTEMS AND METHODS FOR REDUCING MEASUREMENT ERROR USING OPTICAL FIBER SHAPE SENSORS." The contents of each of the above-listed applications are incorporated by reference herein in their entirety.

FIELD

The present disclosure is directed to systems and methods for reducing measurement error in a shape sensing optical fiber, and more particularly to systems and methods for reducing measurement error using shape sensing optical fibers in medical instruments.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert medical instruments to reach a target tissue location. To reach the target tissue location, the minimally invasive medical instruments may navigate natural or surgically created passageways in anatomical systems such as the lungs, the colon, the intestines, the kidneys, the heart, the circulatory system, or the like. Navigational assist systems help the clinician route the medical instruments and avoid damage to the anatomy. These systems can incorporate the use of shape sensors to more accurately describe the shape, position, orientation, and pose of the medical instrument in real space or with respect to pre-procedural or concurrent images. The accuracy and precision of these shape sensors may be compromised by many factors including twisting of the sensor, temperature variations, the location of the shape sensor within the instrument, and axial loading on the sensor.

Improved systems and methods are needed for increasing the accuracy and precision of navigational assist systems, including supplementing the shape sensing capability and the positional accuracy of the shape sensing optical fiber. The devices, systems, and methods disclosed herein overcome one or more of the deficiencies of the prior art.

SUMMARY

The embodiments of the invention are summarized by the claims that follow below.

In one embodiment, an apparatus comprises an instrument including an elongated, flexible body and a shape sensor including an optical fiber extending at least partially along the elongated, flexible body. The apparatus also includes a radiopaque material incorporated with the optical fiber at least partially along a length of the optical fiber.

According to another embodiment, a method of using a shape sensing apparatus during a procedure on a patient comprises obtaining a pre-operative image of target anatomy within the patient before the procedure and extracting a data set from the pre-operative image. The method also includes inserting an instrument into the patient. The instrument includes a shape sensor disposed along an elongated shaft. The shape sensor includes an elongated optical fiber extending within the elongated shaft and incorporates a radiopaque material along at least a portion of the elongated optical fiber. The method also includes obtaining an intra-operative image of the elongated optical fiber as the instrument advances into the patient and correlating the intra-operative image of the elongated optical fiber with the pre-operative image of the target anatomy. The method also includes deducing the position and orientation of the instrument with respect to the target anatomy based upon the correlation and navigating the instrument to the target anatomy.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4A illustrates a perspective, partially cut-away view of the optical fiber shape sensor, and FIG. 4B illustrates a cross-sectional view of the optical fiber shape sensor across the lines 4B-4B shown in FIG. 4A.

FIG. 5A illustrates a perspective, partially cut-away view of the optical fiber shape sensor, and FIG. 5B illustrates a cross-sectional view of the optical fiber shape sensor across the lines 5B-5B shown in FIG. 5A.

FIG. 6A illustrates a perspective, partially cut-away view of the optical fiber shape sensor, and FIG. 6B illustrates a cross-sectional view of the optical fiber shape sensor across the lines 6B-6B shown in FIG. 6A.

DETAILED DESCRIPTION

Figure 1:
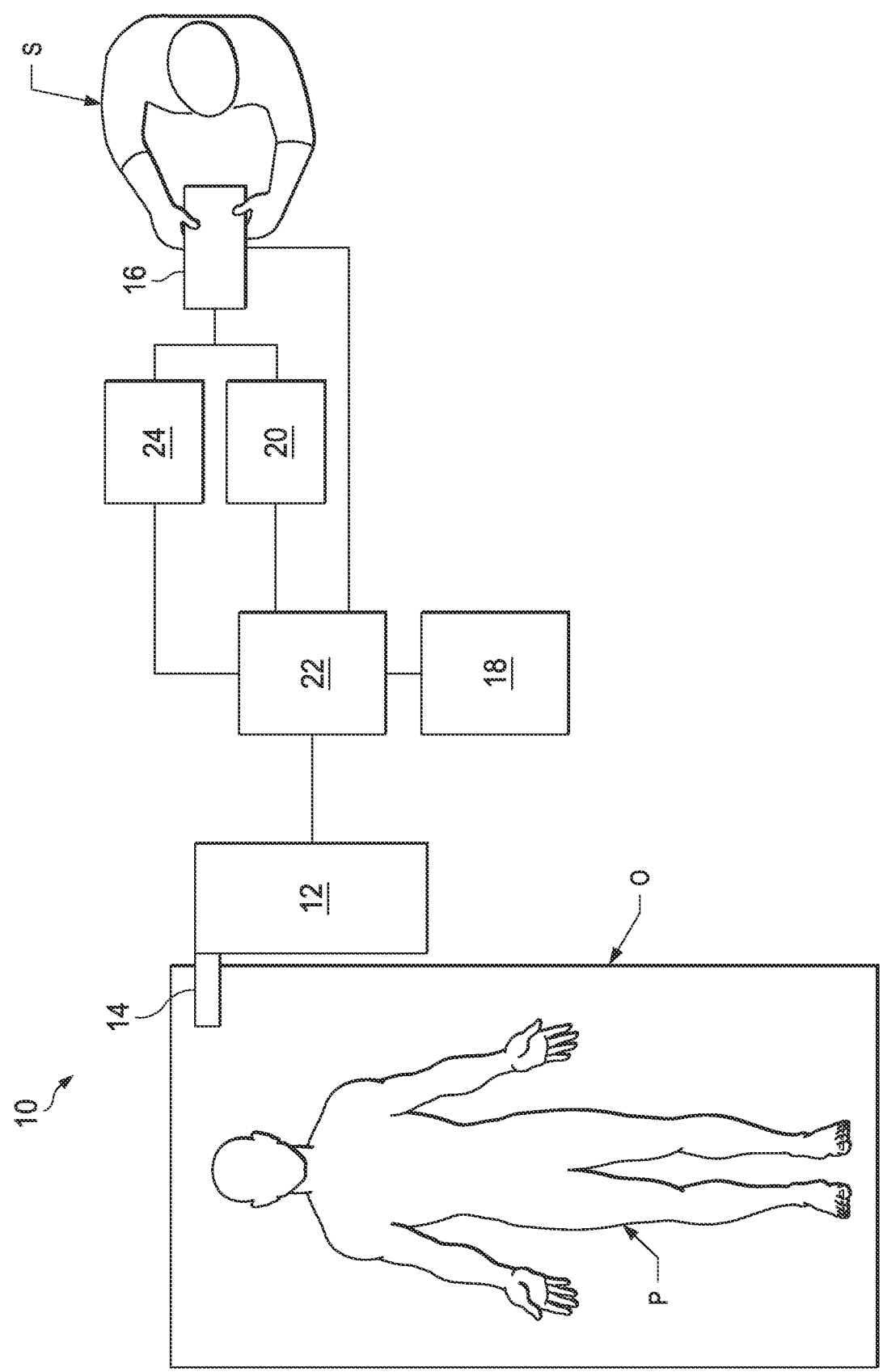
FIG. 1 illustrates an exemplary teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the disclosure.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or processes described with respect to one embodiment may be combined with the features, components, and/or processes described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical site. The term "proximal" refers to the portion of the instrument closer to the clinician, and the term "distal" refers to the portion of the instrument further away from the clinician and closer to the surgical site. For conciseness and clarity, spatial terms such as "horizontal," "vertical," "above," and "below" may be used herein with respect to the drawings. However, medical instruments are used in many orientations and positions, and there terms are not intended to be limiting and absolute.

The present disclosure relates generally to using shape sensor systems to monitor, estimate, and/or predict the shape and/or position of medical instruments used in a variety of medical procedures, including without limitation diagnostic, surgical, and/or therapeutic procedures. In particular, in some embodiments, the shape sensor systems disclosed herein rely on the ability to obtain and interpret optical data from optical shape sensor fibers coupled to a flexible body of a medical instrument while supplementing such optical data with radiographic data (e.g., fluoroscopic shape data) about the optical shape sensor fibers themselves. In particular, some embodiments of the present disclosure are related to shape and/or position tracking by radiographically observing the shape and position of the shape sensing optical fiber to supplement the shape and positional data obtained from the optical fiber while the operator uses the medical instrument during a minimally invasive procedure. In some embodiments, the shape sensing systems may be coupled to a teleoperational medical system. The embodiments disclosed herein may enhance the positional and shape assessment capabilities of shape sensing systems coupled to teleoperational medical systems by radiographically monitoring the shape and position of the shape sensing fibers themselves during manipulation of the medical instruments. Utilizing a radiopaque optical fiber shape sensor may provide better accuracy and precision in location and position tracking than using a radiopaque marker on the catheter system itself. In particular, some embodiments described herein utilize radiopaque structures such as, by way of non-limiting example, radiopaque cladding, radiopaque buffer layers, and/or radiopaque fiber jackets to cover or coat the shape sensing optical fiber cores coupled to the body of the medical instrument. In some instances, by providing additional data about the shape and position of the optical fiber itself, such radiopaque covering or coatings minimize the need to incorporate additional positional sensing (e.g., an EM positional sensor) within the medical instrument to confirm or supplement the optical data provided by the shape sensing optical fiber.

Those of skill in the art will realize that the shape sensing systems disclosed herein may be utilized in similar (e.g., non-teleoperational) applications benefiting from more accurate shape and/or position sensing. By utilizing the shape sensing systems and methods disclosed herein, a user may experience more intuitive and more efficient interaction with the medical instruments and other components coupled to a teleoperational medical system.

According to various embodiments, minimally invasive medical procedures may be performed using a teleoperational system to guide instrument delivery and operation. Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 10 generally includes a teleoperational assembly 12 near or mounted to an operating table O on which a patient P is positioned. The teleoperational assembly 12 may be referred to as a patient-side manipulator (PSM). A medical instrument system 14 is operably coupled to the teleoperational assembly 12. An operator input system 16 allows a surgeon or other type of clinician S to view images of or representing the surgical site and to control the operation of the medical instrument system 14. The operator input system 16 may be referred to as a master or surgeon's console. One example of a teleoperational surgical system that can be used to implement the systems and techniques described in this disclosure is a da Vinci.®. Surgical System manufactured by Intuitive Surgical, Inc. of Sunnyvale, Calif.

The teleoperational assembly 12 supports the medical instrument system 14 and may include a kinematic structure of one or more non-servo controlled links (e.g., one or more links that may be manually positioned and locked in place, generally referred to as a set-up structure) and a teleoperational manipulator. The teleoperational assembly 12 includes plurality of motors that drive inputs on the medical instrument system 14. These motors move in response to commands from a control system 22. The motors include drive systems which when coupled to the medical instrument system 14 may advance the medical instrument into a natural or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument.

The teleoperational medical system 10 also includes an image capture system 18 which includes an image capture or imaging device, such as an endoscope, and related image processing hardware and software. The imaging device may be integrally or removably coupled to the medical instrument system 14. Additionally or alternatively, a separate imaging device that is attached to a separate manipulator assembly may be used with the medical instrument system to image the surgical site.

The teleoperational medical system 10 also includes a control system 22 that is operatively linked to sensors, motors, actuators, and other components of the teleoperational assembly 12, the operator input system 16, and the image capture system 18. The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. More specifically, in response to the surgeon's input commands, the control system 22 effects servomechanical movement of medical instrument system 14. The control device(s) may include one or more of any number of a variety of input devices, such as hand grips, joysticks, trackballs, data gloves, trigger-guns, hand-operated controllers, foot-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The system operator sees images, captured by the image capture system 18, presented for viewing on a display system 20 operatively coupled to or incorporated into the operator input system 16. The display system 20 displays an image or representation of the surgical site and medical instrument system(s) 14 generated by sub-systems of the image capture system 18. The display system 20 and the operator input system 16 may be oriented so the operator can control the medical instrument system 14 and the operator input system 16 with the perception of telepresence. The display system 20 may include multiple displays such as separate right and left displays for presenting separate images to each eye of the operator, thus allowing the operator to view stereo images.

Alternatively or additionally, display system 20 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images. The image may be, for example, a two dimensional (2D) or three dimensional (3D) image captured by an imaging device such as an endoscope positioned within the surgical site. In some embodiments, the display system 20 may display a virtual navigational image in which the actual location of a medical instrument is dynamically referenced with preoperative images to present the surgeon S with a virtual image of a surgical site at the location of the tip of the medical instrument. An image of the tip of the medical instrument or other graphical or alphanumeric indicators may be superimposed on the virtual image to assist the surgeon controlling the medical instrument. The display system 20 may be implemented as hardware, firmware, software, or a combination thereof which interact with or are otherwise executed by one or more computer processors, which may include the processors of the control system 22.

The control system 22 includes at least one memory and at least one processor (not shown), and typically a plurality of processors, for effecting control between the teleoperational system 12, the medical instrument system 14, the operator input system 16, the image capture system 18, and the display system 20. The control system 22 also includes programmed instructions (e.g., a computer-readable medium storing the instructions) to implement some or all of the methods described in accordance with aspects disclosed herein. While the control system 22 is shown as a single block in the simplified schematic of FIG. 1, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, the control system 22 supports wireless communication protocols such as Bluetooth, IrDA, HomeRF, IEEE 802.11, DECT, and Wireless Telemetry.

In some embodiments, the control system 22 may include one or more servo controllers that receive force and/or torque feedback from the medical instrument system 104. Responsive to the feedback, the servo controllers transmit signals to the operator input system 16. The servo controller(s) may also transmit signals instructing the teleoperational assembly 12 to move the medical instrument system(s) 14 which extend into an internal surgical site within the patient body via openings in the body. Any suitable conventional or specialized servo controller may be used. A servo controller may be separate from, or integrated with, the teleoperational assembly 12. In some embodiments, the servo controller and the teleoperational assembly are provided as part of a teleoperational arm cart positioned adjacent to the patient's body.

The teleoperational medical system 10 may further include optional operation and support systems 24 such as illumination systems, eye tracking systems, steering control systems, irrigation systems, and/or suction systems. These systems may be operatively coupled to or incorporated into the operator input system 16. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
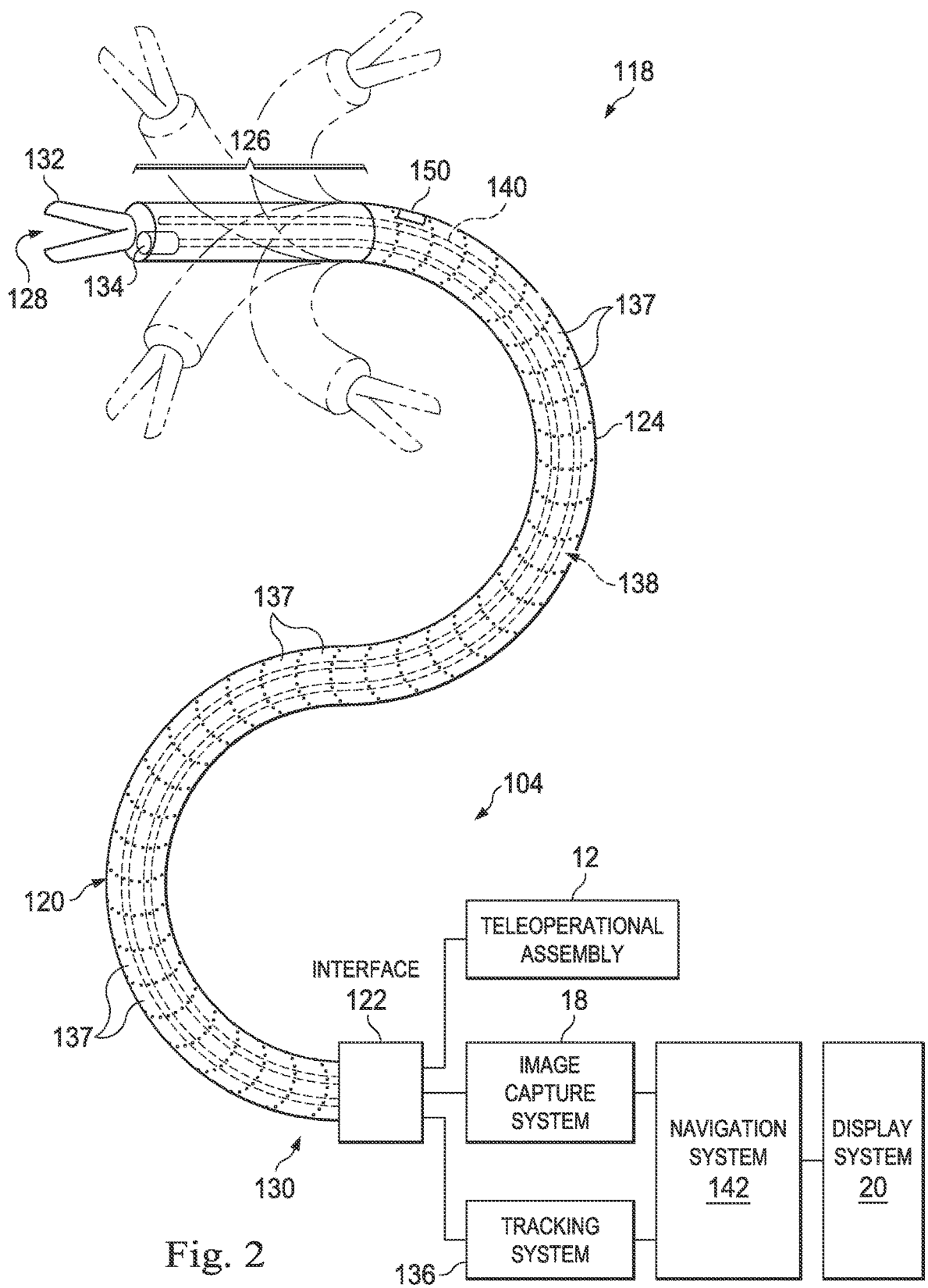
FIG. 2 illustrates a medical instrument system utilizing aspects of the teleoperational medical system according to one embodiment of the present disclosure.

FIG. 2 illustrates a shape sensing apparatus 118 which includes the medical instrument system 14 and its interfacing systems. The medical instrument system 14 includes a steerable instrument 120 coupled by an interface 122 to the teleoperational assembly 12 and the image capture system 18. In the embodiment of FIG. 2, the instrument 118 is teleoperated within the teleoperational medical system 10. In an alternative embodiment, the teleoperational assembly 12 may be replaced by direct operator control. In the direct operation alternative, various handles and operator interfaces may be included for hand-held operation of the instrument.

The instrument 120 has a flexible body 124, a steerable tip 126 at its distal end 128, and the interface 122 at its proximal end 130. The body 124 houses cables, linkages, or other steering controls (not shown) that extend between the interface 122 and the tip 126 to controllably bend or turn the tip as shown for example by the dotted line versions of the bent tip 126, and in some embodiments control an optional end effector 132. The end effector 132 is a working distal part that is manipulable for a medical function, e.g., for effecting a predetermined treatment of a target tissue. For instance, some end effectors have a single working member such as a scalpel, a blade, or an electrode. Other end effectors such as the embodiment of FIG. 2, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, treatments requiring fluid delivery, accessory introduction, biopsy extraction and the like). In other embodiments, flexible body 124 can define one or more lumens through which medical instruments can be deployed and used at a target surgical location.

The instrument 120 can also optionally include an image capture element 134 which may include a stereoscopic or monoscopic camera disposed at the distal end 128 for capturing images that are transmitted to and processed by the image capture system 18 for display by the display system 20. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum.

A tracking system 136 interfaces with a sensor system 138 for determining the shape (and optionally, pose) of the distal end 128 and or one or more segments 137 along the instrument 120. Although only an exemplary set of segments 137 are depicted in FIG. 2, the entire length of the instrument 120, between the distal end 128 and the proximal end 130 and including the tip 126 may be effectively divided into segments, the shape (and location, pose, and/or position) of which may be determined by the sensor system 138. The tracking system 136 may be implemented as hardware, firmware, software or a combination thereof which interact with or are otherwise executed by one or more computer processors, which may include the processors of the control system 22.

The sensor system 138 includes an optical fiber shape sensor 140 aligned with the flexible body 124 (e.g., provided within an interior channel (not shown) or mounted externally). The tracking system 136 is coupled to a proximal end (not shown) of the optical fiber shape sensor 140. In this embodiment, the optical fiber shape sensor 140 has a diameter of approximately 200 µm. In other embodiments, the dimensions may be larger or smaller.

The optical fiber shape sensor 140 forms a fiber optic bend sensor for determining the shape of the instrument 120. In one example, optical fibers including Fiber Bragg Gratings (FBG) are used to provide strain measurements in structures in one or more dimensions. Various systems and methods for monitoring the shape and relative position of an optical fiber in three dimensions are described in U.S. Patent Application Publication No. 2006/0013523, filed on Jul. 13, 2005, U.S. Provisional Patent Application Ser. No. 60/588,336, filed on Jul. 16, 2004, and U.S. Pat. No. 6,389,187, filed on Jun. 17, 1998, the disclosures of which are incorporated herein in their entireties. In other alternatives, sensors employing other strain sensing techniques such as Rayleigh scattering, Raman scattering, Brillouin scattering, and Fluorescence scattering may be suitable. In other alternative embodiments, the shape of the instrument 120 may be determined using other techniques. For example, if the history of the instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument.

The optical fiber shape sensor 140 is used to monitor the shape of at least a portion of the instrument 120. More specifically, light passing through the optical fiber shape sensor 140 is processed by the tracking system 136 for detecting the shape of the medical instrument 120 and for utilizing that information to assist in medical procedures.

The tracking system 136 may include a detection system for generating and detecting the light used for determining the shape of the instrument 120. This information, in turn, in can be used to determine other related variables, such as velocity and acceleration of the parts of the instrument 120. By obtaining accurate measurements of one or more of these variables in real time, the controller can improve the accuracy of the teleoperational medical system and compensate for errors introduced in driving the component parts. The sensing may be limited only to the degrees of freedom that are actuated by the teleoperational medical system, or may be applied to both passive (e.g., unactuated bending of the rigid members between joints) and active (e.g., actuated movement of the instrument) degrees of freedom.

The information from the tracking system 136 may be sent to a navigation system 142 where it is combined with information from the image capture system 18 and/or the preoperatively taken images to provide the surgeon or other operator with real-time position information on the display system 20 for use in the control of the instrument 120. The navigation system 142 may be part of the control system 22 shown in FIG. 1. Alternatively, the navigation system 142 may be part of the optional systems 24 shown in FIG. 1. The navigation system 142 and/or the control system 22 may utilize the position information as feedback for positioning the instrument 120. Various systems for using fiber optic sensors to register and display a medical instrument with surgical images are provided in U.S. patent application Ser. No. 13/107,562, entitled "Medical System Providing Dynamic Registration of a Model of an Anatomical Structure for Image-Guided Surgery," which is incorporated by reference herein in its entirety.

In some embodiments, a series of positional sensors, such as electromagnetic (EM) sensors, positioned along the instrument can additionally or alternatively be used for shape sensing. A history of data from a positional sensor, such as an EM sensor, on the instrument during a procedure may be used to represent the shape of the instrument, particularly if an anatomical passageway is generally static. For example, in the pictured embodiment, the shape sensing apparatus 118 includes a position and orientation sensor 150 (e.g., an electromagnetic (EM) sensor system) which may be disabled by an operator or an automated system (e.g., a function of the control system 22) if it becomes unreliable due to, for example, magnetic interference from other equipment in the surgical suite or if other navigation tracking systems are more reliable. The position sensor 150 may be an EM sensor system that includes one or more conductive coils that may be subjected to an externally generated electromagnetic field. Each coil of the EM sensor system 150 then produces an induced electrical signal having characteristics that depend on the position and orientation of the coil relative to the externally generated electromagnetic field. In one embodiment, the EM sensor system may be configured and positioned to measure six degrees of freedom ("6-DOF"), e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety. In the pictured embodiment, the position sensor 150 is shown positioned within the body 124 near the distal end 128 of the instrument 120. In other embodiments, the position sensor 150 may be positioned at any of a variety of locations along, inside, or outside of the instrument 120. In some embodiments, the position sensor 150 may be used to supplement or confirm the optical data relayed by the optical fiber shape sensor 140. Other embodiments may lack a positional sensor altogether.

Figure 3:
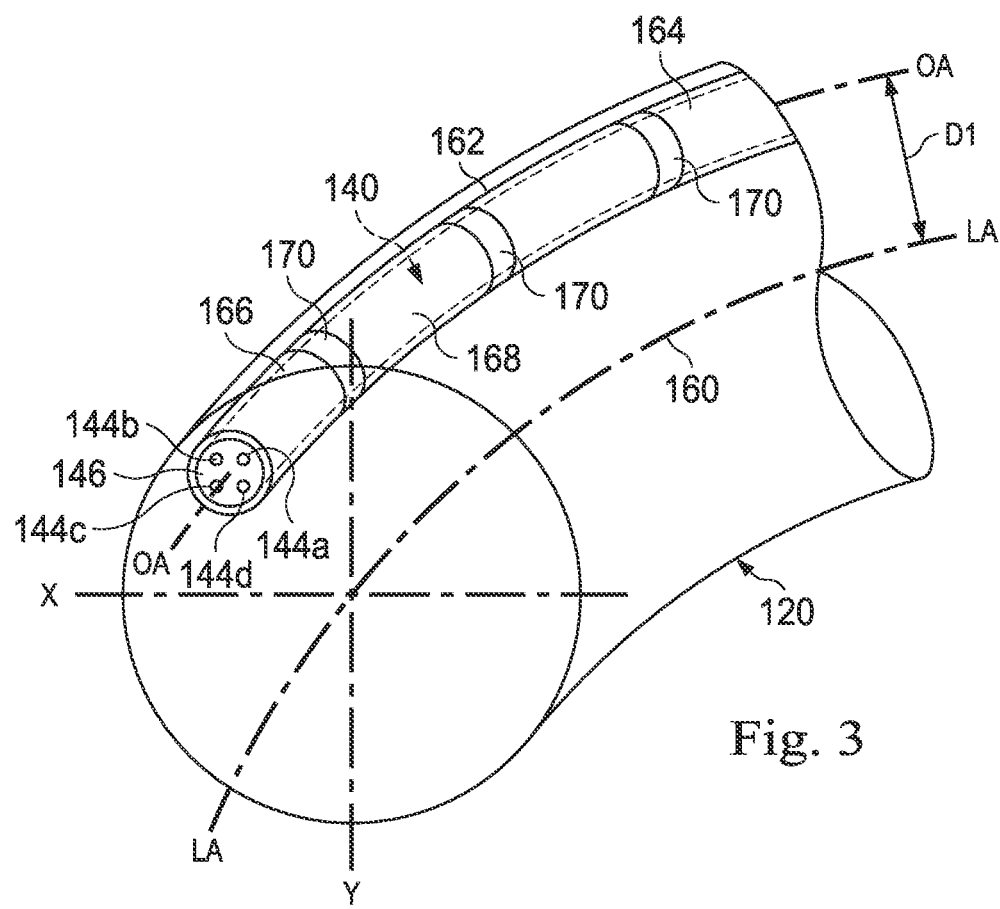
FIG. 3 is a cross-sectional view of a medical instrument including an optical fiber shape sensor according to one embodiment of the present disclosure.

FIG. 3 is a cross-sectional view of the steerable instrument 120 including the optical fiber shape sensor 140 according to one embodiment of the present disclosure. To simplify the illustration, details of the steering components and visual imaging system have been omitted. The illustration is not drawn to scale. The pictured embodiment shows only one optical fiber shape sensor 140 running through the instrument 120, but other embodiments may include multiple optical fiber shape sensors. In this embodiment, the optical fiber shape sensor 140 comprises four cores 144a-144d contained within a single cladding 146. In some embodiments, each core may be single-mode with sufficient distance and cladding separating the cores such that the light in each core does not interact significantly with the light carried in other cores. In other embodiments, the number of cores may vary, the cores may be multimodal, or each core may be contained in a separate optical fiber. In the embodiment of FIG. 3, the fiber cores 144a-d are arranged with approximately 90.degree. spacing about the center of the optical fiber shape sensor 140. In other embodiments, four cores may be arranged with one core in the center of the fiber and three cores spaced at 120.degree. intervals about the center. Other embodiments may include any number of cores. For example, some embodiments include three cores spaced at 120.degree. intervals about the center.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBGs, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065, which is incorporated by reference herein in its entirety.

The optical fiber shape sensor 140 may provide shape data to the tracking system 136 shown in FIG. 2 in the form of strain data. Additionally, strain data may be supplemented with data related to twist errors, light response, temperature errors, or other data that may contribute to determining shape. When applied to a multicore fiber, bending of the optical fiber 140 induces strain on the cores 144a-d that can be measured by monitoring the wavelength shifts in each core. By having two or more cores disposed off-axis in the fiber (e.g., relative to the longitudinal axis OA), bending of the fiber 140 induces different strains on each of the cores 144*a*-*d*. These strains are a function of the local bend radius of the fiber 140, the radial position of the individual core with respect to the fiber centerline (e.g., about the longitudinal axis OA) and the angular position of the core about the core centerline with respect to the plane of fiber bending. For example, strain induced wavelength shifts in regions of the cores containing FBGs located at points where the fiber is bent, can thereby be used to determine the amount of bending at those points. These data, combined with the known spacings of the FBG regions along the length of the optical fiber shape sensor 140, can be used to reconstruct the shape of the fiber 140. Such a system has been described by Luna Innovations. Inc. of Blacksburg, Va.

In the embodiment shown in FIG. 3, the optical fiber shape sensor 140 includes the four optical cores 144*a*-144*d* disposed at equal radial distances from and equal angular intervals about the longitudinal axis OA of the optical fiber shape sensor 140 such that in cross-section, opposing pairs of cores 144*a*-144*c* and 144*b*-144*d* form orthogonal axes. The sensing locations along the four optical cores are aligned such that measurements from each core are from substantially correlated axial regions along the optical fiber 140 (axial refers to the fiber orientation, not the spacing). The fiber cores 144 may include multiple FBGs or sets thereof that are axially distributed along each core 144*a*-144*d*. In various embodiments, the FBGs may be continuous, overlapping or partially overlapping. For example, in one embodiment, each core 144*a*-144*d* includes an array of collinear FBGs that are disposed at known positions along the lengths of each core 144*a*-144*d* such that the FBGs 144*a*-*d* for all four cores 144*a*-144*d* are longitudinally aligned (e.g., with respect to distance from the distal end 128 of the medical instrument 120) at a plurality of sensor segments 137, including the steerable tip 126.

A bending of the optical fiber shape sensor 140 in one of the sensor segments 137 will lengthen at least one core 144*a*-144*d* with respect to the opposing core 144*a*-144*d*. Interrogation of this length differential along the fiber enables the angle and radius of bending to be extracted. This interrogation may be performed using the tracking system 136. There are a variety of ways of multiplexing the FBG's so that a single fiber core can carry many sensors and the readings of each sensor can be distinguished. Some of the various ways are described in U.S. patent application Ser. No. 13/049,012, which is incorporated by reference herein in its entirety. For example, in some embodiments, the tracking system 136 and/or the navigation system 142 comprises a bend sensing system that includes an optical to electronic signal processing subsystem (e.g., an interrogator) that injects laser light into the optical fiber shape sensor 140 and processes the reflected light from the FBGs to calculate the local bend radius and bend direction of the optical fiber shape sensor 140.

As mentioned above, in alternative embodiments, optical fibers with fewer or more cores may be used Likewise, the fiber cores may be arranged in different patterns, such as, by way of non-limiting example, a central core with additional cores spaced at angular intervals around the central core. In one embodiment, a hollow utility channel may provide access for removable devices including removable medical instruments, removable steering components, removable visualization components or the like. In some embodiments, the instrument body 124 may include an internal channel or fiber lumen sized to accommodate the optical fiber 140 and separate it from the steering or visualization components, which themselves may be accommodated through separate channels. In FIG. 3, for example, the optical fiber shape sensor 140 is positioned within a fiber lumen 162. The fiber lumen 162 may extend throughout the length of the medical instrument 120.

In FIG. 3, the optical fiber shape sensor 140 is centered at a radial distance D1 from a neutral axis 160 that in this embodiment extends longitudinally through the instrument 120 along a longitudinal axis LA of the instrument. The neutral axis 160 is the axis of the instrument 120 along which little or no axial strains (due to tension, twist, or compression) occur during bending. In other embodiments, the optical fiber shape sensor 140 may be positioned at or along the neutral axis 160. In alternative embodiments, the optical fiber shape sensor 140 (and the fiber lumen 162) may be centered about the neutral axis 160 or located at a different radial distance. In this embodiment, the optical fiber shape sensor 140 may be offset from the neutral axis 160 to accommodate other components of the instrument 120 such as cables or other steering components or visualization components (not shown) that may be centered on or clustered about the neutral axis 160. In this embodiment, the neutral axis 160 extends generally along the central axis of the instrument 120. In alternative embodiments, the optical fiber shape sensor 140 may be positioned within the instrument 120 (e.g., within the fiber lumen 162) at other distances from the neutral axis or at other angular displacements from the neutral axis.

When the optical fiber shape sensor 140 is positioned offset from the neutral axis, the optical fiber shape sensor 140 is subject to axial tensile and compressive forces during bending which strain all of the fiber cores and may contribute to bending measurement error. Twist in the optical fiber shape sensor 140 may cause strain or stress on the optical fiber shape sensor 140 (e.g., in addition to the strain caused by the bending of the medical instrument 120) that contributes to bending measurement error. Unless the data from the FBGs can be parsed into identifiable components of reflected optical readings from stress or strain due to bending and reflected optical readings from stress or strain due to twist or torsion, the displacement information determined from the optical data can include inaccuracy or error in estimating the position or shape of the medical instrument 120.

Accordingly, in order to accurately estimate or predict the position or shape of the elongate medical instrument 120 as discussed above using the optical fiber shape sensor 140, it may be helpful to monitor the position and shape of the optical fiber shape sensor 140 as a whole during manipulation (e.g., steering and/or bending) of the medical instrument 120. In the embodiments described herein, a radiopaque component is incorporated into or located adjacent to the optical fiber shape sensor 140 and may improve the accuracy of determining the position and orientation of the shape sensor and the flexible medical instrument 120 in the body of a patient. Errors in the calculated shape of the optical fiber shape sensor 140 and the medical instrument 120 carrying it may be corrected in real-time during the procedure by reference to another source of shape information, e.g., a fluoroscopic image of the optical fiber shape sensor 140. The radiopaque element or component of the radiopaque optical fiber shape sensor 140 is aligned along the longitudinal axis OA of the optical fiber shape sensor 140. As will be described in detail below, the aligned radiopaque element may be concentric with the optical fiber shape sensor longitudinal axis OA or may be otherwise generally parallel to the longitudinal axis OA. The radiopaque characteristics of the optical fiber shape sensor 140 are generally sufficiently different from the radiopaque characteristics of the instrument 120 to enable the controller (e.g., the user or automated controller) to visually distinguish the position and orientation of the optical fiber shape sensor 140 from the position and orientation of the instrument 120. Thus, the radiographic contrast between the optical fiber shape sensor 140 and the instrument 120 is sufficiently great to enable identification and monitoring of the position and orientation of the optical fiber shape sensor 140 distinct from the position and orientation of the instrument 120. In this way, the radiopaque optical fiber shape sensor 140 may allow the user to compensate for or disregard the anatomical deformation of the instrument 120 in evaluating the position and orientation of the optical fiber shape sensor 140.

In some instances, the optical fiber shape sensor 140 is radiopaque along the entire length of the optical fiber shape sensor 140. In some instances, the optical fiber shape sensor 140 is radiopaque from a proximal portion 164 to a distal portion 166 of the fiber. In other instances, discrete portions of the optical fiber shape sensor 140 are radiopaque while other portions are not. For example, in some instances, only the distal portion 166 of the optical fiber shape sensor 140 is radiopaque. In some embodiments, different sections or lengths of the optical fiber shape sensor 140 may include varying types or amounts of radiopacity or radiographic contrast. For example, in some embodiments, the optical fiber shape sensor 140 may include separate bands 170 of similar or differing radiopacity. The bands 170 may be generally parallel to and concentric with the longitudinal axis OA of the sensor 140 and may be spaced at different longitudinal positions along the length of the optical fiber shape sensor 140. The bands 170 may be useful in 2D applications to provide depth indication. In some embodiments, the proximal portion 164, a midportion 168, and the distal portion 166 may display increasing radiopacity (e.g., as a gradual gradient-type increase from the proximal portion 164 to the distal portion 166, or with areas of abrupt demarcation between the proximal portion 164, the midportion 168, and the distal portion 166 (e.g., the bands 170). Such variations in radiographic characteristics along the length of the optical fiber shape sensor 140 may allow different sections of the optical fiber shape sensor to be identified and monitored visually and/or may allow for use with different imaging modalities. For example, in some instances, a more radiopaque proximal portion 164 may highlight the contrast at the body entry (e.g., the proximal portion 164 may incorporate barium sulfate to highlight the entry of the instrument into the patient).

Figure 4A:
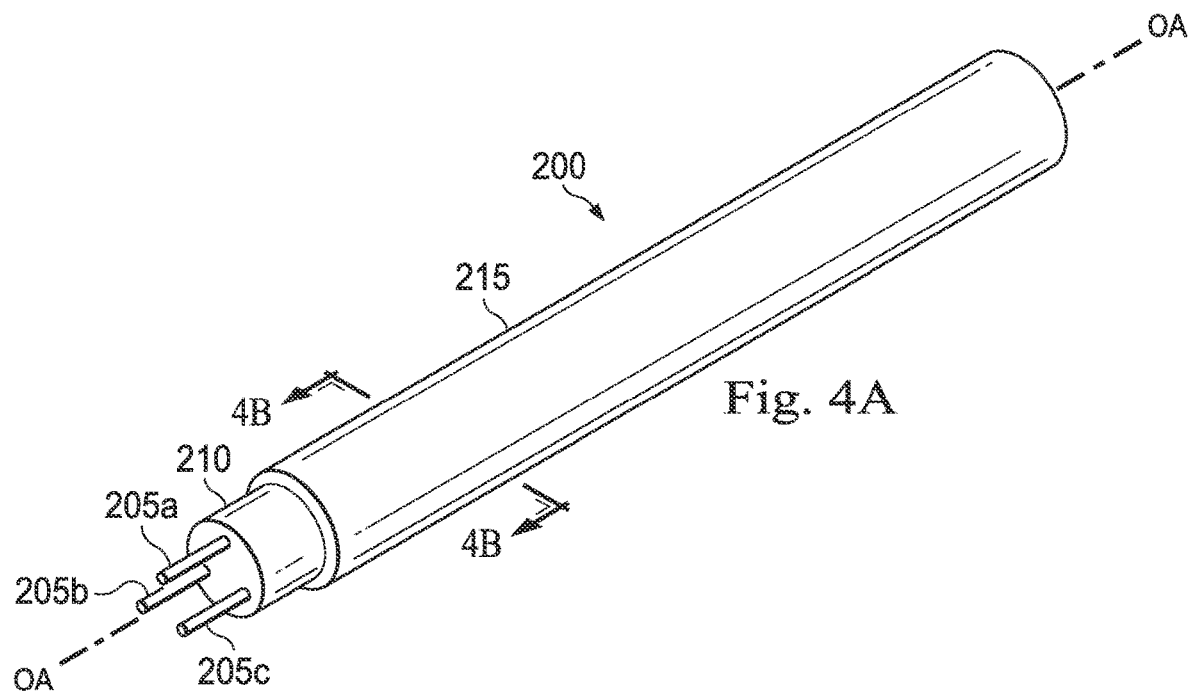
FIGS. 4A and 4B illustrate an exemplary optical fiber shape sensor according to one embodiment of the present disclosure.
Figure 4B:
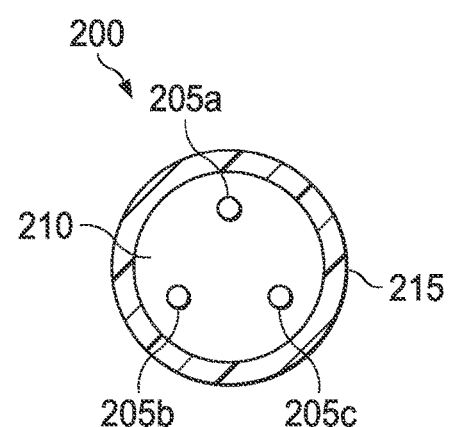

FIGS. 4A and 4B illustrate an exemplary optical fiber shape sensor 200 according to one embodiment of the present disclosure. FIG. 4A illustrates a perspective, partially cut-away view of the optical fiber shape sensor 200, and FIG. 4B illustrates a cross-sectional view of the optical fiber shape sensor 200 across the lines 4B-4B shown in FIG. 4A. The optical fiber shape sensor 200 may be the same as the optical fiber shape sensor 140 described above in relation to FIGS. 2 and 3. The optical fiber shape sensor 200 comprises three cores 205*a-c* surrounded by a cladding 210, which is sheathed by a buffer 215. Each core 205*a-c* comprises a single continuous strand of glass or plastic that forms the physical medium that transports fiber optic data signals. In the pictured embodiment, the cores 205*a-c* comprise light conducting fiber optic waveguides that may be similar to the cores described in U.S. Pat. No. 7,781,724 filed Sep. 26, 2006, disclosing "Fiber Optic Position and Shape Sensing Device and Method Relating Thereto," which is incorporated by reference herein in its entirety. Each core 205*a-c* runs the length of the optical fiber shape sensor 200 with light reflecting FBGs written at intervals along the length of the core. In the embodiment shown in FIG. 4B, the cores 205*a-c* are spaced approximately 120 degrees apart. In the pictured embodiment, the cores 205*a-c* extend substantially parallel to each other within the cladding 210 along a longitudinal axis OA of the optical fiber shape sensor 200.

The cladding 210 forms a cylindrical layer of optical material surrounding the cores 205*a-c*, and the cladding 210 functions to "trap" the light within the cores through the optical technique known as "total internal reflection." The cladding extends generally parallel to and may be concentric with the longitudinal axis OA. Typically, the cores 205*a-c* are designed to have a higher index of refraction, an optical parameter that is a measure of the speed of light in the material, than the cladding 205, which causes "total internal reflection" to trap light in the core up to a certain angle, which defines the numerical aperture of the fiber. In some embodiments, the cores 205*a-c* and the cladding 210 comprise ultra-pure silica glass with or without germanium doping.

Typical cores and claddings are invisible to radiographic imaging (e.g., fluoroscopy), which limits the ability of the controller/user to monitor the position of optical fiber shape sensor independent of the fiber optical data relayed by the shape sensor. Even through the optical fiber shape sensor may extend through a medical instrument that includes radiographically visible portions (e.g., radiopaque markers), the precise location and orientation of the optical fiber shape sensor cannot be determined via similar imaging. In accordance with the principles of the present disclosure, however, the optical fiber shape sensor itself may be impregnated, coated, or otherwise marked with radiopaque material to allow the controller (e.g., the user or automated controller) to monitor and evaluate the precise location and orientation of the optical fiber shape sensor via imaging. The radiographic data obtained from the radiographic imaging of the optical fiber shape sensor itself can then be correlated or compared to the shape and position data relayed by the optical fiber shape sensor to enhance the accuracy and precision of the fiber optical data obtained by the optical fiber shape sensor. In some embodiments, the cores are individually surrounded by distinct sheaths of radiopaque material. In some embodiments, the cladding is impregnated with radiopaque material. In some embodiments, the buffer is impregnated with radiopaque material. Other embodiments include a radiopaque jacket or sheath surrounding the buffer layer. For embodiments in which the cladding is impregnated with radiopaque material, the radiopaque material may be chosen to permit total internal reflection.

In the pictured embodiment, for example, the cladding 210 is formed of a silica-based glass that is doped with a compound having radiopaque properties. For example, by way of non-limiting example, the silica-based glass of the cladding 210 may be doped with a compound of barium, bismuth tungsten, iodine, or another radiopaque material (e.g., Au, Ta, Y, Nb, Mo, Pb, Ru, Rh, La, Ce, Pr, Nd, Sm, Eu, Gd, Tb, Dy, Ho, Er, Tm, Yb, Lu, Hf, Ta, Re, Os, Jr, Th, and U). In some instances, the radiopaque material may have similar features to the radiopaque markers described in U.S. Patent Publication No. 2007/0191708 A1 to Gerold et al., entitled "Radio-opaque Marker for Medical Implants," PCT filed Mar. 31, 2004, which is incorporated by reference in its entirety herein. Thus, the cladding 210 of the pictured embodiment is visible on imaging (e.g., through radiographic or fluoroscopic imaging).

In other embodiments, the cladding may be formed of a polymer compound blended with a radiopaque agent (e.g., a radiopaque polymeric material). In some instances, the radiopaque polymeric material of either the buffer or the cladding may have similar features to the radiopaque polymer blends and radiopaque polymer salt complexes described in the article "Radiopaque Polymeric Materials for Medical Research: Current Aspects of Biomedical Research," published in Investigative Radiology, Vol. 34 (5), May 1999, which is incorporated by reference in its entirety herein. To obtain the desired refractive index of the core and the claddings, other elements can be added.

The buffer 215 of the optical fiber shape sensor 200 forms a cylindrical tube circumferentially surrounding the cladding 210 and generally parallel to and concentric with the longitudinal axis OA of the sensor. The buffer 215 protects the cladding 210 and the cores 205a-c from moisture and physical damage. In accordance with the principles of the present disclosure, the buffer 215 may be fabricated to have radiopaque properties that assist the user/controller in monitoring the position and/or orientation of optical fiber shape sensor 200 via imaging. In particular, the buffer 215 may be additionally or alternatively impregnated (e.g., doped) with a compound having radiopaque properties. For example, by way of non-limiting example, the buffer 215 may be doped with a compound of barium, bismuth tungsten, iodine, or another radiopaque material (e.g., Au, Ta, Y, Nb, Mo, Pb, Ru, Rh, La, Ce, Pr, Nd, Sm, Eu, Gd, Tb, Dy, Ho, Er, Tm, Yb, Lu, Hf, Ta, Re, Os, Jr, Th, and U). In other embodiments, the buffer 215 may be formed of a polymer compound blended with a radiopaque agent (e.g., a radiopaque polymeric material), as described above in relation to the cladding 210. For example, in one embodiment, the buffer 215 may be formed of a polymer compound such as, by way of non-limiting example, acrylate compounded with a radiopaque material such as barium sulfate, bismuth oxychloride (or other bismuth compounds), tungsten metal powder, iodine compounds, a thin deposited coating of gold, or any of the other radiopaque materials listed above.

The cladding 210 and/or the buffer 215 may be fabricated to have radiopaque characteristics that distinguish the optical fiber shape sensor 200 from the remaining structures within the medical instrument (e.g., the medical instrument 120 shown in FIG. 3). In some embodiments, the cladding 210 and the buffer 215 may be fabricated to have radiopaque characteristics that distinguish them from each other. For example, the cladding 210, the buffer 215, and the medical instrument may have different radiographic characteristics that allow them to be distinguished on imaging.

Figure 5A:
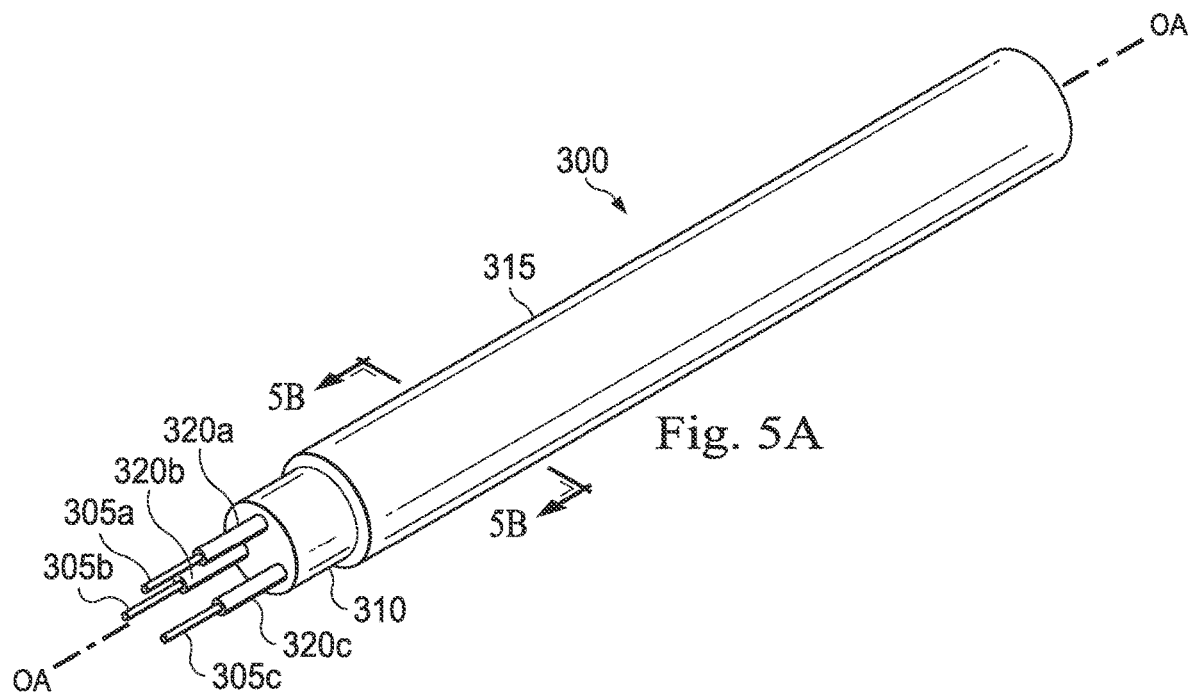
FIGS. 5A and 5B illustrate an exemplary optical fiber shape sensor according to one embodiment of the present disclosure.
Figure 5B:
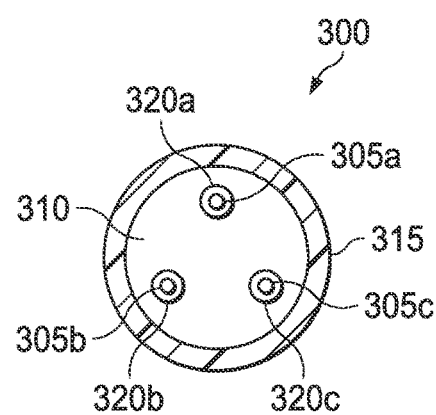

In some embodiments, as illustrated in FIGS. 5A and 5B, the optical fiber shape sensor may include a boundary layer adjacent the fiber cores to maintain an adequate index of refraction difference between the cladding and the cores, which ensures that light propagation is confined within the cores. FIGS. 5A and 5B illustrate an exemplary optical fiber shape sensor 300 according to one embodiment of the present disclosure. FIG. 5A illustrates a perspective, partially cut-away view of the optical fiber shape sensor 300, and FIG. 5B illustrates a cross-sectional view of the optical fiber shape sensor 300 across the lines 5B-5B shown in FIG. 5A. The optical fiber shape sensor 300 may be the same as the optical fiber shape sensor 200 described above in relation to FIGS. 4A and 4B. The optical fiber shape sensor 300 comprises three cores 305a-c surrounded by a cladding 310, which is sheathed by a buffer 315. In some instances, the buffer 315 may be impregnated with radiopaque materials as described above in relation to the buffer 215 shown in FIGS. 4A and 4B. The buffer 315 extends generally parallel to and is generally concentric with the longitudinal axis OA of the sensor 300. Each core 305a-c is surrounded by a boundary layer 320a-c, respectively. In some embodiments, the boundary layers 320a-c are formed of pure silica glass.

Figure 6A:
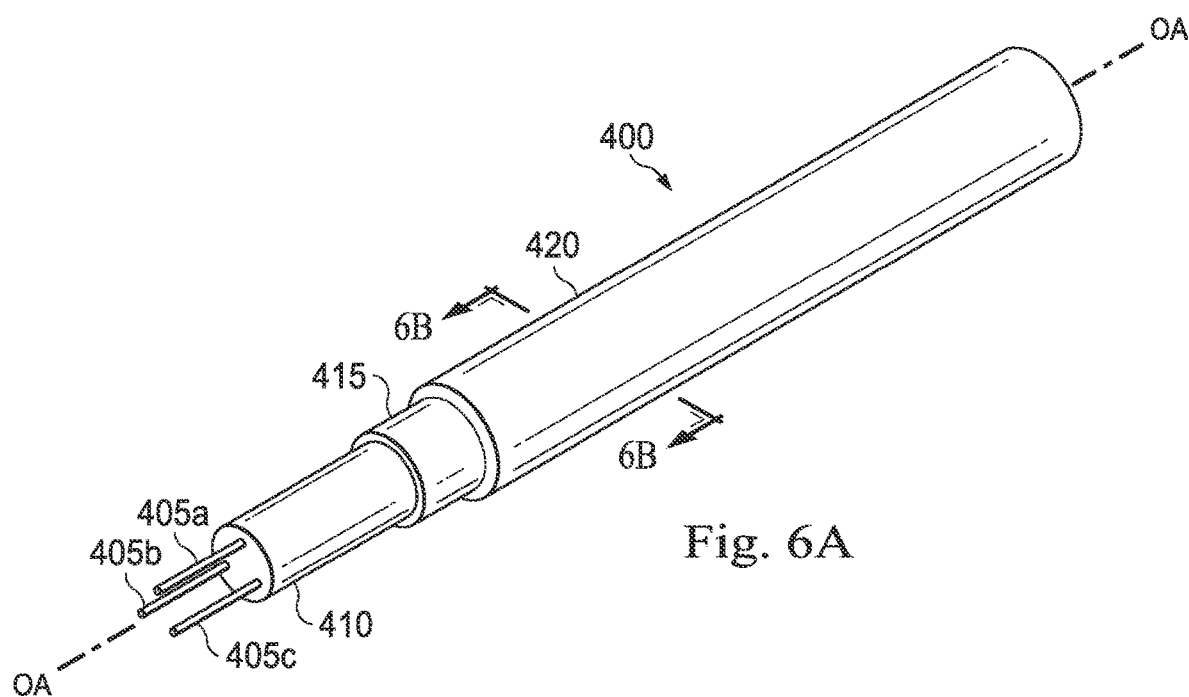
FIGS. 6A and 6B illustrate an exemplary optical fiber shape sensor according to one embodiment of the present disclosure.
Figure 6B:
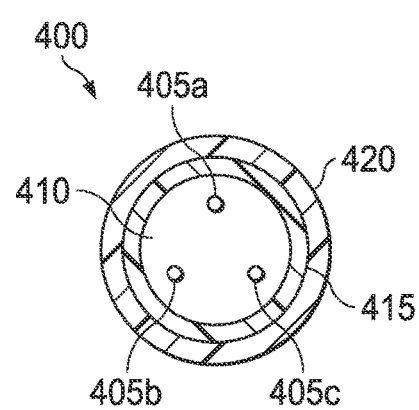

In some embodiments, as illustrated in FIGS. 6A and 6B, the optical fiber shape sensor may be embedded within or covered by a tube or tubular jacket that includes radiopaque characteristics. FIGS. 6A and 6B illustrate an exemplary optical fiber shape sensor 400 according to one embodiment of the present disclosure. FIG. 6A illustrates a perspective, partially cut-away view of the optical fiber shape sensor 400, and FIG. 6B illustrates a cross-sectional view of the optical fiber shape sensor 400 across the lines 6B-6B shown in FIG. 6A. The optical fiber shape sensor 400 may be the same as the optical fiber shape sensor 200 described above in relation to FIGS. 4A and 4B. The optical fiber shape sensor 400 comprises three cores 405a-c surrounded by a cladding 410, a buffer 415, and a jacket 420. In some instances, the buffer 415 may be impregnated with radiopaque materials as described above in relation to the buffer 215 shown in FIGS. 4A and 4B. The buffer 415 extends generally parallel to and is generally concentric with the longitudinal axis OA of the sensor 400. In the pictured embodiment, the jacket 420 forms a cylindrical tube comprising radiopaque materials. For example, by way of non-limiting example, the jacket 420 may be doped with a compound of barium, bismuth tungsten, iodine, or another radiopaque material (e.g., Au, Ta, Y, Nb, Mo, Pb, Ru, Rh, La, Ce, Pr, Nd, Sm, Eu, Gd, Tb, Dy, Ho, Er, Tm, Yb, Lu, Hf, Ta, Re, Os, Jr, Th, and U). In some embodiments, the jacket 420 may be formed of stainless steel (e.g., stainless steel hypodermic tubing), wire-wound coil tubing, braided tubing, and/or tubing made of any of a variety of radiopaque materials. In some embodiments, the jacket 420 may be formed of a polymer compound blended with a radiopaque agent (e.g., a radiopaque polymeric material), as described above.

Figure 7:
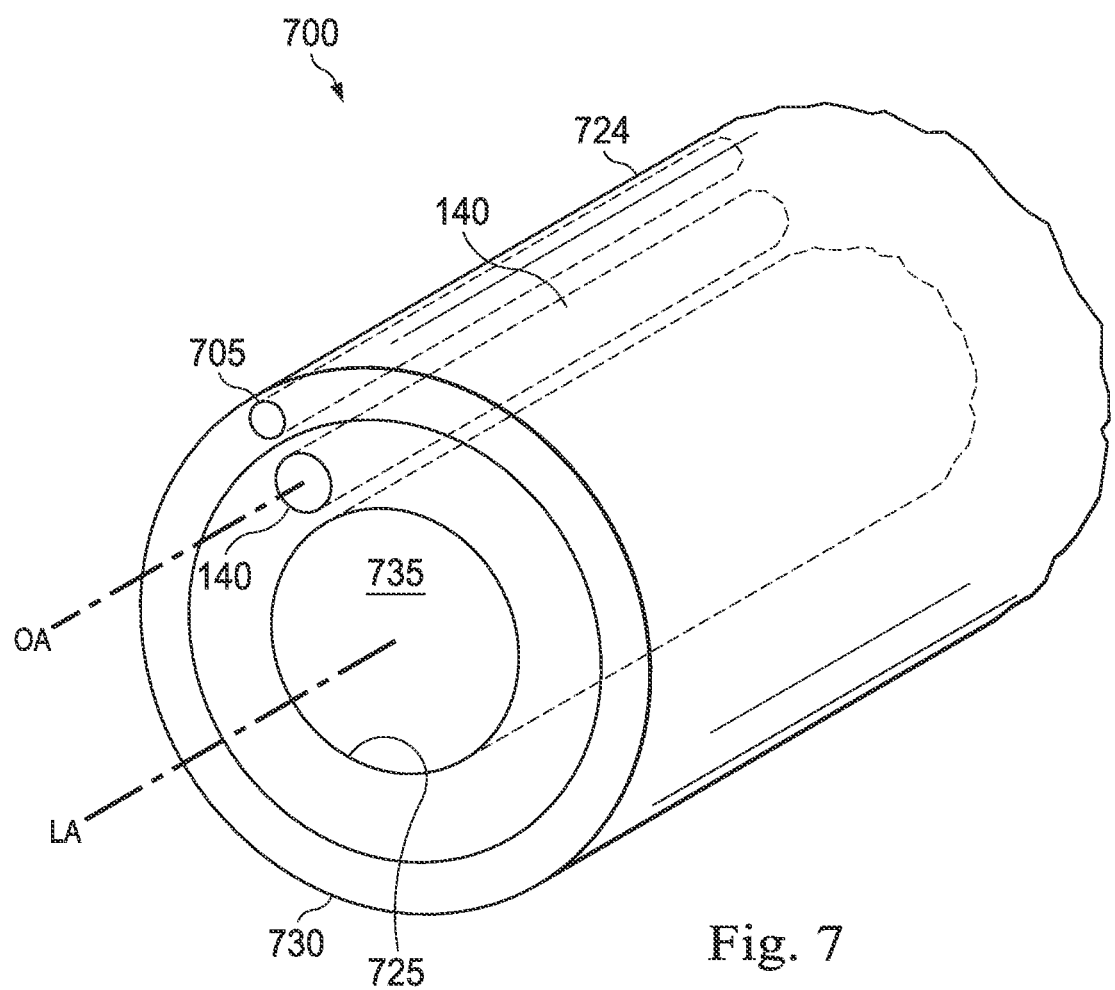
FIG. 7 illustrates a perspective view of an exemplary medical instrument including an exemplary radiopaque element and an exemplary optical fiber shape sensor according to one embodiment of the present disclosure.

In some embodiments, as illustrated in FIG. 7, an exemplary medical instrument 700 may be constructed or formed with a radiopaque element 705 that is angularly aligned (i.e., at the same angular orientation relative to the longitudinal axis LA) with the optical fiber shape sensor 140 relative to the longitudinal axis of the medical instrument 700. The medical instrument 700 may be substantially similar to the medical instrument 120 shown in FIG. 2. The instrument 700 may include a fiber lumen (not shown) extending through a flexible body 724 (which may be similar to the flexible body 124 shown in FIG. 2) that is configured to carry the optical fiber shape sensor 140. In the pictured embodiment, the body 724 forms an elongate, flexible tube having an inner surface 725 and an outer surface 730. The inner surface 725 of the body 724 defines a central lumen 735. The central lumen 735 may comprise the working channel of the instrument 700. The instrument 700 may include other components (not shown) such as position sensors, actuation members, or other components as described for FIG. 2. In other embodiments, the optical fiber shape sensor 140 can be coupled, bonded or attached to the inner surface 725 or to the outer surface 730 as appropriate. The inner surface 725 may also define a groove in which the optical fiber shape sensor 140 may be positioned. In yet other embodiments, the optical fiber shape sensor 140 can be coupled to or integral with the outer surface 730 using, for example, a suitable adhesive or bonding agent, and/or the optical fiber shape sensor 140 may be positioned within an aperture or groove that is formed within the outer surface 730. Further, the optical fiber 140 can be coupled to the instrument 700 in such a manner that a portion of the optical fiber 140 is coupled at a known reference location on the proximal portion of the instrument 700. In FIG. 7, the radiopaque element 705 may be co-extruded with the materials of a flexible body 724 of the medical instrument 700 to align with the angular orientation of the optical fiber shape sensor 140 extending along the length of the medical instrument 700. In other embodiments, the radiopaque element 705 may be coupled directly to the optical fiber shape sensor 140 along its length or coupled to the fiber lumen along its length. In still other embodiments, the radiopaque element 705 may have a different angular orientation than the sensor 140 but may be adjacent to or in the near vicinity of the sensor to provide a radiopaque marker for the sensor. In these various embodiments, the radiopaque element 705 extends generally parallel to the longitudinal axis OA of the sensor 140.

Figure 8:
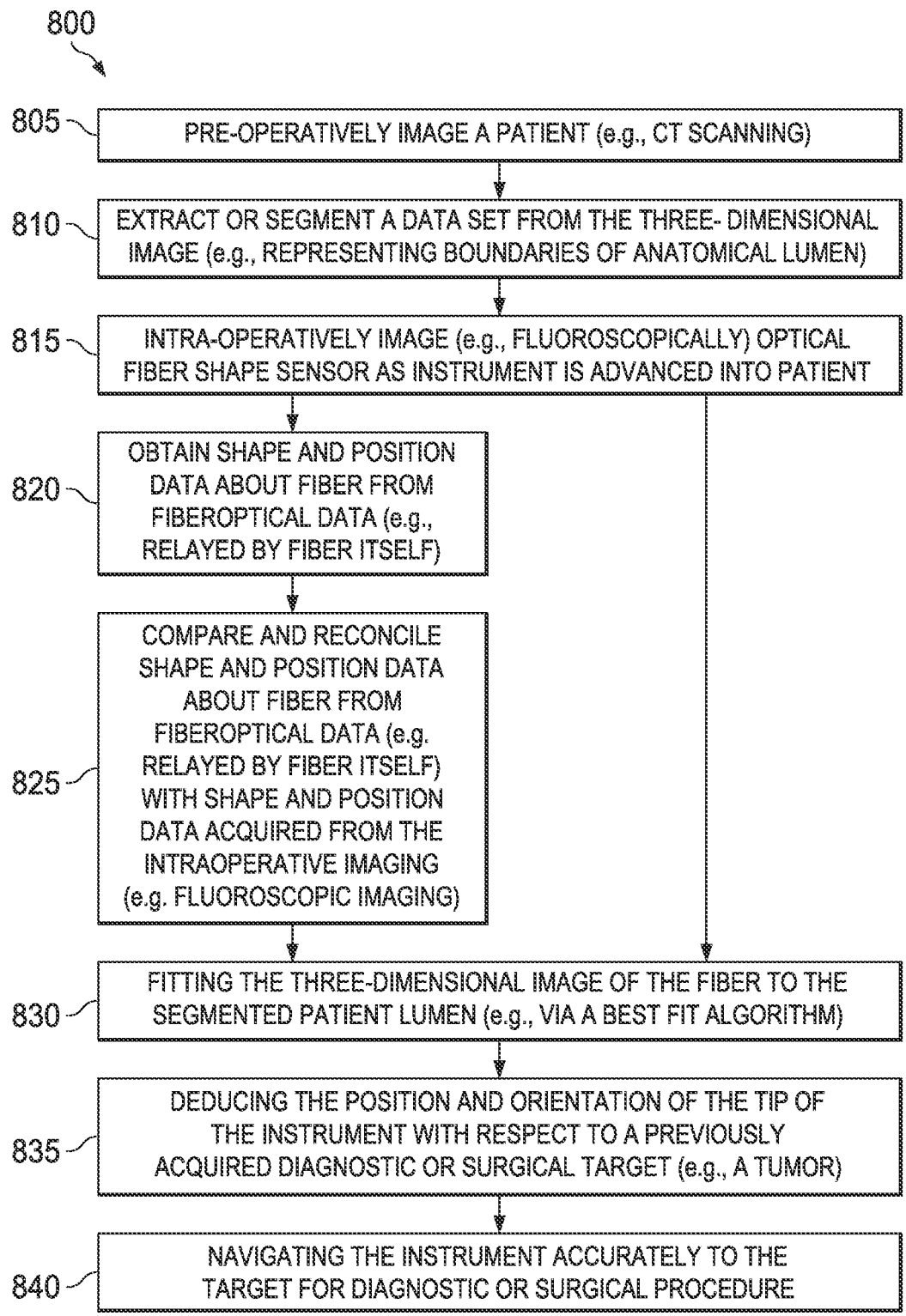
FIG. 8 is a flow diagram illustrating an exemplary method of using a medical instrument including a radiopaque optical fiber shape sensor according to one embodiment of the present disclosure.

FIG. 8 depicts a flowchart 800 illustrating an exemplary method of using a medical instrument utilizing a radiopaque optical fiber shape sensor described herein. At process 805, a controller may pre-operatively image a patient to obtain baseline images of the patient's anatomical structures of interest (e.g., bronchial passageways of the lung). In some embodiments, the controller may obtain preoperative images using computerized tomography (CT) scanning. At process 810, a data set may be extracted or segmented from the preoperative images (e.g., 3D image set) representing the relevant boundaries of the patient anatomy (e.g., the luminal boundaries of the patient passageways). At process 815, the controller may intra-operatively image the patient as the medical instrument carrying the radiopaque optical fiber shape sensor (e.g., the optical fiber shape sensor 140 described above) is advanced into the patient anatomy (e.g., using real-time fluoroscopic imaging during the procedure).

In some embodiments, at optional process 820, the teleoperational medical system (e.g., the teleoperational medical system 10 shown in FIG. 1 and/or the tracking system 136 shown in FIG. 2) obtains fiber optical data from the radiopaque optical fiber shape sensor that reflects shape and position data about the fiber and the medical instrument. For example, in some embodiments, optical sensors on the fluoroscopic system (e.g., a C-arm portion of the fluoroscope) provide the pose of the C-arm, and the teleoperational medical system can determine the shape and location of the optical fiber shape sensor (e.g., the position of the proximal end of the shape sensor) relative to the pose of the C-arm. At optional process 825, the teleoperational medical system compares and reconciles the shape and positional data obtained from the optical fiber shape sensor itself with the shape and positional data acquired from the intraoperative imaging of the radiopaque optical fiber shape sensor (e.g., the fluoroscopically-acquired real-time shape/position information). In some embodiments, the teleoperational medical system may combine data from at least three sources to ultimately determine the position and orientation of the medical instrument within the patient anatomy—namely, the pre-operatively obtained image data about the patient anatomy, the intra-operatively obtained fiber optical data from the radiopaque optical fiber shape sensor, and the intra-operatively obtained imaging data about the radiopaque optical fiber shape sensor itself.

In other embodiments, the teleoperational medical system does not obtain or evaluate fiber optical data from the radiopaque optical fiber shape sensor that reflects shape and position data about the fiber and the medical instrument. For example, in some instances, the teleoperational medical system may perform process 830 and match the radiopaque optical fiber shape sensor to the pre-operatively acquired image of the patient anatomy (e.g., image of patient lumens) by a best sit algorithm without the necessity of fiber optic shape sensing. As mentioned above in relation to FIG. 2, some embodiments may employ an EM positional sensor to supplement the navigational accuracy of the radiopaque optical fiber shape sensor data in guiding the progress of the medical instrument through the patient anatomy. However, in some instances, the teleoperational medical system may fit the 3D image of the radiopaque optical fiber shape sensor to the segmented patient lumen data without the necessity of fiber optic shape sensing or EM sensing of the position and orientation of points along the flexible body of the medical instrument. Such functionality can be useful in situations where the medical instrument lacks an EM positional sensor, and/or where the optical fiber shape sensor is non-functional or turned OFF. In other embodiments, the teleoperational system uses the fiber optical data acquired by the radiopaque optical fiber shape sensor to supplement the navigational process before arriving at process 830, as highlighted by processes 820 and 825.

At process 835, the teleoperational medical system determines or deduces the position and orientation of the medical instrument (e.g., the distal tip of the medical instrument) relative to a previously acquired diagnostic or surgical target (e.g., a tumor or other lesion within the patient anatomy). In some instances, the target is visible on the pre-operatively acquired imaging. At process 840, the teleoperational medical system and/or the controller advances or navigates the instrument accurately to the target to perform the diagnostic or surgical procedure (such as, without limitation, imaging, biopsy, therapeutic ablation, surgical excision or removal).

The embodiments described herein describe optical fiber shape sensors having radiopaque characteristics, and, in particular, optical fiber shape sensors having incorporated (e.g., impregnated or coated) radiopaque materials. The embodiments described herein allow the teleoperational medical system and/or the controller to supplement the shape sensing capability, the positional accuracy, and the fit to the pre-operatively acquired image of patient anatomy (e.g., the segmented lung airway model) of the radiopaque shape sensing optical fiber with intra-operatively acquired fluoroscopic shape information about the radiopaque shape sensing optical fiber itself. Thus, the radiopaque characteristics of the shape sensors described herein can enhance the shape sensing capability of an optical fiber shape sensor through intermittent or real time sampled intra-operative imaging (e.g., via fluoroscopic imaging) of the instrument carrying the optical fiber shape sensor as it travels within a patient.

Although the optical fiber shape sensors and positional sensor systems have been described herein with respect to teleoperated or hand operated surgical systems, these sensors can find application in a variety of medical and non-medical instruments in which accurate instrument bending measurements could be compromised by displacements of the shape sensors relative to the medical instruments (e.g., rotational displacement and/or linear displacement).

One or more elements in embodiments of the invention may be implemented in software to execute on a processor of a computer system such as control system 108. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An apparatus comprising:
   an instrument comprising:
      an elongated, flexible body including an inner surface and an outer surface, wherein the inner surface is shaped to define a lumen extending through at least a portion of the elongated, flexible body; and
      a plurality of portions extending along a length of the elongated, flexible body;
   a shape sensor extending at least partially along the elongated, flexible body; and
   one or more radiopaque materials incorporated into a first portion of the plurality of portions and a second portion of the plurality of portions such that the first portion has a first radiopacity and the second portion has a second radiopacity, wherein the first radiopacity is different from the second radiopacity, wherein the first portion includes a first band and the second portion includes a second band, and wherein the first and second bands are spaced at different longitudinal positions along a length of the shape sensor.

2. The apparatus of claim 1, wherein the second portion is distal to the first portion, and wherein the second radiopacity is greater than the first radiopacity.

3. The apparatus of claim 2, wherein the one or more radiopaque materials transition from the first radiopacity to the second radiopacity as a gradient.

4. The apparatus of claim 2, wherein a demarcation area separates the first portion from the second portion, and wherein the one or more radiopaque materials transition from the first radiopacity to the second radiopacity at the demarcation area.

5. The apparatus of claim 2, wherein the one or more radiopaque materials are incorporated into a third portion of the plurality of portions such that the third portion has a third radiopacity, wherein the third radiopacity is lower than the second radiopacity of the second portion and greater than the first radiopacity of the first portion.

6. The apparatus of claim 1, wherein the second portion is distal to the first portion, and wherein the first radiopacity is greater than the second radiopacity.

7. The apparatus of claim 1, wherein a first radiopaque material of the one or more radiopaque materials is incorporated into the first band, and wherein a second radiopaque material of the one or more radiopaque materials is incorporated into the second band.

8. An apparatus comprising:
   an instrument comprising:
      an elongated, flexible body including an inner surface and an outer surface, wherein the inner surface is shaped to define a lumen extending through at least a portion of the elongated, flexible body; and
      a plurality of portions extending along a length of the elongated, flexible body;
   a shape sensor comprising an optical fiber extending at least partially along the elongated, flexible body; and
   one or more radiopaque materials incorporated into a first portion of the plurality of portions and a second portion of the plurality of portions such that the first portion has a first radiopacity and the second portion has a second radiopacity, wherein the first radiopacity is different from the second radiopacity.

9. The apparatus of claim 8, wherein the optical fiber comprises the first and second portions of the plurality of portions and wherein the first and second portions are impregnated with the one or more radiopaque materials.

10. The apparatus of claim 8, wherein the optical fiber comprises at least one core embedded within a cladding, wherein the cladding comprises the first and second portions of the plurality of portions.

11. The apparatus of claim 10, wherein each of the first and second portions is doped with the one or more radiopaque materials.

12. The apparatus of claim 8, wherein the optical fiber comprises a buffer surrounding a cladding, wherein the buffer comprises the first and second portions of the plurality of portions.

13. The apparatus of claim 8, wherein the optical fiber comprises a radiopaque jacket, and wherein the radiopaque jacket comprises the first and second portions of the plurality of portions.

14. The apparatus of claim 13, wherein the radiopaque jacket comprises at least one of stainless steel tubing, braided tubing, or coiled tubing.

15. The apparatus of claim 1, wherein a radiopaque element comprises the one or more radiopaque materials, wherein the radiopaque element is within the elongated, flexible body and is parallel to a longitudinal axis of the elongated, flexible body.

16. The apparatus of claim 15, wherein the shape sensor comprises an optical fiber extending at least partially along the elongated, flexible body, and wherein the radiopaque element is aligned with an angular orientation of the shape sensor.

17. A method, comprising:
   receiving a pre-operative image of a target anatomy within a patient;
   extracting a data set from the pre-operative image;
   receiving an intra-operative image of at least a portion of an elongated, flexible body of an instrument as the instrument is inserted into the patient, wherein one or more radiopaque materials are incorporated into a first portion and a second portion of the elongated, flexible body such that the first portion has a first radiopacity and the second portion has a second radiopacity, wherein the first radiopacity is different from the second radiopacity;

correlating the intra-operative image of the at least the portion of the elongated, flexible body with the pre-operative image of the target anatomy;

based on the correlating, determining a position and orientation of the instrument with respect to the target anatomy; and determining a navigation path for the instrument to advance to the target anatomy.

18. The method of claim 17, wherein the instrument includes a shape sensor comprising an elongated optical fiber, and wherein receiving the intra-operative image of at least the portion of the elongated, flexible body comprises receiving an intra-operative image of at least a portion of the elongated optical fiber.

19. The method of claim 18, wherein the one or more radiopaque materials are incorporated with the elongated optical fiber along at least a portion of the elongated optical fiber.

20. The method of claim 18, further comprising:

receiving shape data from the shape sensor;

generating an instrument bend measurement based on the received shape data; and comparing the received shape data from the shape sensor with shape data associated with the intra-operative image of at least the portion of the elongated optical fiber.

* * * * *